United States Patent
Albanna et al.

(10) Patent No.: US 12,351,620 B1
(45) Date of Patent: Jul. 8, 2025

(54) PROCESS FOR PRODUCTION OF A SOLUBLE AND INSOLUBLE COLLAGEN PRODUCT FROM MAMMALIAN DERMIS TISSUE

(71) Applicant: Humabiologics, Inc., Phoenix, AZ (US)

(72) Inventors: Mohammad Z. Albanna, Chandler, AZ (US); Nilabh S. Kajave, Tempe, AZ (US)

(73) Assignee: Humabiologics, Inc., Phoenix, AZ (US)

( * ) Notice: Subject to any disclaimer, the term of this patent is extended or adjusted under 35 U.S.C. 154(b) by 0 days.

(21) Appl. No.: 18/935,623

(22) Filed: Nov. 3, 2024

Related U.S. Application Data

(63) Continuation-in-part of application No. 18/654,723, filed on May 3, 2024, now Pat. No. 12,134,792.

(60) Provisional application No. 63/463,579, filed on May 3, 2023.

(51) Int. Cl.
| | |
|---|---|
| *C09H 3/02* | (2006.01) |
| *A61K 38/39* | (2006.01) |
| *A61K 47/42* | (2017.01) |
| *C07K 14/78* | (2006.01) |
| *C11B 1/10* | (2006.01) |
| *C12N 9/26* | (2006.01) |

(52) U.S. Cl.
CPC ............ *C07K 14/78* (2013.01); *C12N 9/2414* (2013.01); *C12Y 302/01001* (2013.01)

(58) Field of Classification Search
CPC .. C09H 3/02; C11B 1/10; C07K 14/78; A61K 47/42; A61K 38/39; A61L 15/32; A61L 15/325
See application file for complete search history.

(56) References Cited

U.S. PATENT DOCUMENTS

| | | | |
|---|---|---|---|
| 4,784,986 A | 11/1988 | Usher | |
| 4,969,912 A | 11/1990 | Kelman et al. | |
| 5,677,284 A | 10/1997 | Li | |
| 5,980,946 A | 11/1999 | Jones et al. | |
| 6,936,271 B1 | 8/2005 | Oliver et al. | |
| 10,709,810 B2 | 7/2020 | Sun et al. | |
| 10,821,205 B2 | 11/2020 | Xu et al. | |
| 2007/0014773 A1 | 1/2007 | Matheny et al. | |
| 2015/0313623 A1 | 11/2015 | Bellomo et al. | |
| 2019/0247287 A1 | 8/2019 | Pinsky | |
| 2019/0351097 A1 | 11/2019 | Voytik-Harbin | |
| 2020/0093799 A1 | 3/2020 | Dreher | |
| 2022/0168472 A1* | 6/2022 | Bose | A61K 38/40 |

FOREIGN PATENT DOCUMENTS

| | | | |
|---|---|---|---|
| CA | 2101637 | * | 7/1993 |

OTHER PUBLICATIONS

U.S. Appl. No. 65/480,177, filed Apr. 15, 2003, Subramanian Gunasekaran.

* cited by examiner

*Primary Examiner* — Maryam Monshipouri
(74) *Attorney, Agent, or Firm* — Invention To Patent Services; Alex Hobson

(57) ABSTRACT

A process for the production of a soluble collagen product and an insoluble collagen product from mammalian dermis tissue is described. The tissue may initially be processed to remove the epidermis and adipose tissue and then minced into small pieces. The process includes washing the minced dermis in an enzymatic solution, such as an amylase solution followed by homogenizing the amylased tissue. The soluble and insoluble collagen is then extracted from the homogenized tissue and subsequently separated into distinct soluble and insoluble fractions. The process produces collagen with high Dalton values that can subsequently be combined to produce a mixed composite collagen product. Also, the extracted collagen may be used as an integral composite collagen before separation.

3 Claims, 2 Drawing Sheets

PROCESS FOR PRODUCTION OF A SOLUBLE AND INSOLUBLE COLLAGEN PRODUCT FROM MAMMALIAN DERMIS TISSUE

CROSS REFERENCE TO RELATED APPLICATIONS

This application is a continuation in part of U.S. patent application Ser. No. 18/654,723, filed on May 3, 2024, and currently pending, which claims the benefit of priority to U.S. provisional patent application No. 63/463,579, filed on May 3, 2023; the entirety of all prior priority applications are hereby incorporated by reference herein.

BACKGROUND OF THE INVENTION

Field of the Invention

The invention relates to a process for the production of a soluble collagen product and an insoluble collagen product from mammalian dermis tissue.

Background

Collagen type I, the most prevalent protein in the human body, possesses a distinct triple helix structure that is composed of two pro-alpha ($\alpha_1$) polypeptide chains and one pro-alpha ($\alpha_2$) chain. This structure is built upon a repeating glycine-X-Y triplet, where X and Y commonly refer to proline and hydroxyproline amino acids. This unique arrangement provides collagen with exceptional biocompatibility, biodegradability, permeability, and fibrillogenesis. Collagen's ubiquitous nature, biological characteristics and ease of processing have allowed for its use in a range of different biomaterials-based applications including grafts and various manufactured products. However, collagen's weak mechanical properties and increased susceptibility to enzymatic degradation remain significant challenges.

SUMMARY OF THE INVENTION

The invention is directed to a process for the production of a soluble collagen product and an insoluble collagen product from mammalian dermis tissue. The process may utilize dermis tissue from any suitable mammal and in particular may use human dermis. The dermis may have adipose tissue as well as epidermis. The tissue may initially be processed to remove the epidermis and adipose tissue using conventional methods. The dermis tissue is preferably minced into small pieces have a maximum size, such as maximum length or width across the plane of the dermis, of no more than about 10 mm, no more than about 5 mm, no more than about 2 mm and any range between and including the minced dermis sizes provided. Smaller minced dermis may be preferred as it may enable faster processing due to the higher surface area of contact with the solutions. The process includes washing the minced dermis in an enzymatic solution, such as an amylase solution followed by homogenizing the amylased tissue. The soluble and insoluble collagen is then extracted from the homogenized tissue and subsequently separated into distinct soluble and insoluble fractions. The process produces collagen with high molecular weights expressed in Dalton values that can subsequently be combined to produce a mixed composite collagen product. Also, the extracted collagen may be used as an integral composite collagen before separation. The extracted collagen may be in an extracted collagen solution having both the soluble and insoluble collagen combined but in different phases within the solution or separated by density or specific gravity within the solution. An extracted collagen solution may undergo centrifugation to physically separate the soluble from the insoluble collagen.

The minced dermis tissue may be washed in a lipid removal solution that is an amylase solution comprising an effective amount of amylase to remove the lipids and soften the tissue for extraction. The amylase solution may have a concentration of amylase from 0.01 mg/ml or more, 0.05 mg/ml or more, 0.1 mg/ml or more, 0.5 mg/ml or more, 1 mg/ml or more, 2 mg/ml or more and any other range between and including the amylase concentration. The amylase may be in a solution with water and may include a buffer, such as a phosphate buffer comprising phosphate. The concentration of phosphate may have a concentration of about 0.001 M or more, 0.01 M or more, 0.1M or more and any other range between and including the phosphate buffer concentration.

An exemplary lipid removal process includes washing the minced dermis tissue in a series of solutions, including a lipid removal solution and an organic solvent solution, such as an ethanol or other alcohol solution. A lipid removal solution may include water, chloroform, organic solvents including, but not limited to, methanol and/or hexane. Other lipid removal solution components may include surfactants, chelants and buffers, wherein the buffer may act as a facilitator to maintain pH. An exemplary buffer may be Phosphate Buffered Saline (PBS) or Tris Base. A lipid removal solution may also include a surfactant, such as an inorganic surfactant, and/or a non-ionic surfactant. An exemplary surfactant is Triton, Ethylenediaminetetraacetic Acid (EDTA). A lipid removal solution may also include an antifoaming agent such as Tributyl phosphate.

The minced dermis tissue may be washed in the lipid removal solution for a wash time of about 8 hours or more, about 10 hours or more about 20 hours or more, about 25 hours or more, about 30 hours or more and any range between and including the wash times.

The lipid removal solution may be cooled during the washing of the minced dermis tissue in the lipid removal solution. The lipid removal solution may be cooled to about 10° C. or less, about 8° C. or less, about 5° C. or less, and any range between and including the temperature values provided.

An exemplary ethanol solution includes ethanol with at least water, wherein the ethanol has a concentration of about 50% or more, about 60% or more, about 70% or more, about 80% or more and any range between and including the values provided, such as from about 60% to 70%, for example.

The minced dermis tissue may be washed in the ethanol solution for a wash time of about 1 hour or more, about 4 hours or more about 10 hours or more, about 16 hours or more, about 24 hours or from about 1 to 30 hours and any range between and including the wash times provided.

The ethanol solution may be cooled during the washing of the minced dermis tissue in the ethanol solution. The ethanol solution may be cooled to about 10° C. or less, about 8° C. or less, about 5° C. or less, and any range between and including the temperature values provided.

The process may wash the minced dermis in each of the organic and inorganic solvents one time each, two times each, three times each and even four times each or more.

The lipid removed dermis tissue is then homogenized while being maintained at a cold temperature to prevent degradation of the collagen, such as no more than 40° C. to produce homogenized tissue. It may be preferred to homogenize the lipid removed dermis tissue at a temperature near but above freezing, such as above freezing but below about 10° C., or below about 8° C., or below about 5° C. Homogenizing may be accomplished by blending, shearing or cutting the lipid-removed tissue.

The lipid-removed tissue is then subject to an extraction solution that utilizes an enzyme to extract the collagen by cleaving the telo regions of the collagen to release the collagen into solution. An exemplary extraction solution may include an enzyme, acid and/or water and/or a pepsin solution. An exemplary pepsin solution may include an acid solution, such as an acetic acid solution combined with pepsin. The acid solution may have a molar concentration of about 0.1 M or more, about 0.5 M or more, about 1.0 M solution or more, about 2 M solution, about 2.5 M solution and any range between and including the molar concentrations provided. The pepsin may include the pepsin solution in a concentration of about 0.25 mg/ml or more, about 0.5 mg/ml or more about 0.75 mg/ml or more and 1.5 M solution or more, about 2 M solution, about 2.5 M solution and any range between and including the concentrations provided.

The lipid-removed tissue may be washed in the extraction solution for an extraction time of about 8 hours or more, about 24 hours or more about 48 hours or more, about 72 hours or more, about 96 hours or more and any range between and including the extraction times.

An exemplary extraction solution may be maintained in a temperature range of about 10° C. or less, about 8° C. or less, about 5° C. or less, and any range between and including the temperature values provided.

The extraction solution is typically agitated during collagen extraction to promote the solubilization of collagen from the extracellular matrix of the tissue source. Agitation helps to break down the tissue and expose the collagen fibers to the extraction solution, which contains acidic solutions to help denature the collagen and extract it from the tissue.

Agitation can help to improve the homogeneity of the collagen solution and reduce the formation of aggregates or clumps of collagen fibers.

Agitation can be achieved using various methods, such as mechanical stirring, shaking, or sonication. The level of agitation can affect the efficiency of collagen extraction, as higher levels of agitation can help to break down the tissue more quickly and increase the contact between the collagen fibers and the extraction solution.

Strong alkaline solution, such as sodium hydroxide solution can help to remove residual lipids, proteins, and other impurities from the tissue surface. This can help to improve the purity and yield of the extracted biomaterial. In addition, alkaline solution can also help to solubilize or denature certain types of extracellular matrix proteins, such as elastin or glycosaminoglycans, which may interfere with the extraction of the desired biomaterial, such as collagen. Alkaline solution treatment can also help to expose or unmask the collagen fibers in the tissue, making them more accessible to subsequent extraction steps. This can improve the efficiency of collagen extraction and help to minimize the use of harsher extraction methods that may damage the collagen fibers or alter their properties.

The soluble and insoluble collagen may then be separated through any conventional means including, but not limited to filtration, centrifugation, and the like.

A soluble collagen product, as defined herein will dissolve in an acid of Molar concentration of about 1 mM or more, about 5 mM or more, about 10 mM solution or more, about 50 mM solution, about 100 mM solution and any range between and including the molar concentrations provided.

An exemplary pH of the solution may be about 0.5 or more, about 1.0 or more, about 1.5 or more, about 2.0 or more, about 3.0 or more, about 4.0 or more and any range between and including the pH values provided.

The soluble collagen may be non-dialyzed collagen, or may be dialyzed to change molecular weight, remove impurities and/or adjust the pH.

The soluble collagen may further be lyophilized, including freezing the collagen and then heating the frozen collagen to a lyophilization temperature of at least 50° C. (70° F.) and drawing vacuum on the collagen; wherein a vacuum pressure is at least 100 mTorr.

An insoluble collagen product, as defined herein can provide a more stable and durable scaffold for cell growth and tissue regeneration, due to its highly crosslinked structure. This can be important in load-bearing applications, such as bone or cartilage tissue engineering, where the scaffold needs to withstand mechanical forces. Insoluble collagen can also have improved resistance to enzymatic degradation.

A composite collagen product may be crosslinked chemically or physically through a chemical crosslinker including, but not limited to, glutaraldehyde, formaldehyde, formalin, genipin, 1-ethyl-3-(3-dimethylaminopropyl) carbodiimide (EDC). A chemical crosslinking may be achieved by immersing the composite collagen product in a solution containing the chemical crosslinker or by exposure to a vapor that includes the chemical crosslinker, which may be done under vacuum to draw the chemical crosslinker into the composite collagen product. In a vapor exposure crosslinking process, the contact distance of the composite collagen product from the surface of the crosslinker solution may be controlled to control the degree of crosslinking. The degree of crosslinking may be controlled by controlling the concentration and volume of chemical crosslinker and the time of exposure and temperature during exposure with the composite collagen product. The time of exposure or time of immersion of the composite collagen product during a crosslinking process may be about 1 minute of more, about 10 minutes or more, about 30 minutes or more, about 45 minutes or more or even about one hour or more and any range between and including the values provided. Chemical crosslinking may be achieved at a controlled temperature and pressure, such as a temperature of about 30° C. or more, about 50° C. or more, about 75° C. or more, about 100° C. or less or from about 30° C. to about 100° C. and any other range between and including the temperatures provided and the crosslinking time, the time at the crosslinking temperature may be varied depending on the mass of the composite collagen and the temperature and may be about 1 minute of more, about 10 minutes or more, about 30 minutes or more, about 45 minutes or more or even about one hour or more and any range between and including the values provided. The pressure may be controlled during a chemical crosslinking process and the absolute pressure during processing may be full vacuum or about 0 mmHg, or about 1 mmHg or more, about 250 mmHg or more, about 500 mmHg or more, about 760 mmHg or more wherein there is positive pressure over atmospheric pressure, such as an absolute pressure of about 1,000 mmHg or more, about 2,000 mmHg or more, about 4,000 mmHg or more or any range between and including the pressure values provided.

A physical crosslinking may be achieved by heating the composite collagen to a crosslinking temperature of about 30° C. or more, about 50° C. or more, about 75° C. or more, about 100° C. or less or from about 30° C. to about 100° C. and any other range between and including the temperatures provided and the crosslinking time, the time at the crosslinking temperature may be varied depending on the mass of the composite collagen and the temperature and may be about 1 minute of more, about 10 minutes or more, about 30 minutes or more, about 45 minutes or more or even about one hour or more and any range between and including the values provided.

Insoluble collagen will be homogenized in water and may be non-dialyzed collagen, or may be dialyzed to change molecular weight, remove impurities and/or adjust the pH. Homogenizing may be accomplished by blending, shearing or cutting the lipid removed tissue.

An insoluble collagen may further be lyophilized, including freezing the collagen and then heating the frozen collagen to a lyophilization temperature of at least 50° C. (70° F.) and drawing vacuum on the collagen; wherein a vacuum pressure is at least 100 m Torr.

The distinct collagen components soluble and insoluble may be collected and further dried and lyophilized. As described herein the two distinct products may be mixed in a ratio to form a mixed composite collagen product. The ratio may be a weight ratio of the soluble collagen component to the insoluble collagen component. This composite collagen product may have an engineered ratio of soluble and insoluble collagen designed for specific applications. The ratio of the soluble and insoluble collagen components in the composite affects the chemical, mechanical and biological properties. The properties that can be tailored by a change in the ratio of the components include, but are not limited to, durometer, or hardness, stiffness, modulus, elongation at break, max load, water absorption, rate of absorption or break down as measured by the rate of weight loss. The ratio of the components can increase or decrease how long it takes for the product to break down. A first ratio of soluble to insoluble components may have a time to reach half an initial max load that is double the time to reach half an initial max load of a second ratio of soluble to insoluble components, as an example.

The ratio of soluble to insoluble collagen by weight may be about 0.25:1 or less, or greater than about 0.25:1, about 0.5:1 or more, about 0.75:1 or more, about 1:1 or more, about 1.25:1 or more, about 1.5:1 or more, about 1.75:1 or more, and any range between and including the ratios provided.

This invention includes a method of controlling the concentration of soluble and insoluble collagen or ratio in a composite collagen product. This method may include separating the components as described herein and then mixing them together in an engineered ratio to provide the chemical, mechanical and biological properties desired.

A composite collagen product may be made into a shaped composite collagen product, a three-dimensional shape or structure or form (with measurable dimensions) such as a sheet, sphere, tube, rod, polygonal shape, or irregular shape. An irregular shape may be configured to interface with an anatomical body part, such as bone, tissue, muscle, organ and the like. A composite collagen product may include a combination of shapes, such as a sphere coupled to rod. A shaped composite collagen product may be a sheet having a thickness of about 0.1 mm to about 10 mm, wherein a membrane may be defined as a thin sheet having a thickness of about 0.1 mm to 1 mm or to about 2 mm. A sheet or membrane is a planar shape having a first side that is generally planar with a second, opposing side. A sheet or membrane may extend an area of about 1 mm$^2$ to about 10,000 cm$^2$.

A collagen product may be particles, which may be made from a collagen sheet or other composite collagen product. The collagen product may be frozen, such as to cryogenic temperatures and then ground or pulverized to produce collagen particles which may particle size of millimeters, or micrometers, for example. The collagen particles may be added to a collagen product as an additive.

A composite collagen may be reconstituted and formed into a flowable solution, which may be injectable through a needle, such as a 26 gauge needle or larger (needle opening size of 0.45 mm). A flowable additive may be added to the composite collagen to form a flowable composition and the additive may be glycerol or collagen solution, for example.

A shaped collagen product may be formed with different properties through the thickness of the sheet or from a first side to a second side. For example, the first side may have a larger pore size or structure than the pore size or structure of a second side. A first side may have a rough texture while a second side may be substantially smoother than said first side. These changes in the structure may be controlled by freezing parameters, molding parameters, composition and structure and materials of the mold, and lyophilization parameters. The mold may have a rough or smooth surface, for example. The collagen fibers in a shaped composite collagen product may be aligned or randomly oriented by controlling the freezing parameters, molding parameters, composition and structure of materials of the mold, and/or lyophilization parameters. A shaped composite collagen product having aligned collagen fibers may be stronger along the oriented axis than a randomly oriented or non-aligned shaped composite collagen product.

A shaped composite collagen product may be oriented, wherein the collagen fibers are oriented, such as being aligned during formation of the shaped composite collagen product, such as while being frozen or formed and shaped, or shaped into a hydrogel. For example, a composite collagen may be extruded and stretched while being frozen to increase the tensile strength of the shaped composite collagen product. A shaped composite collagen product may be formed into a strand by extrusion and may have a diameter of less than about 10 mm, or less than 5 mm or even less than 1 mm, and may further be woven into a fabric wherein the strands are woven one over another. A strand may be an elongated member having a length at least 10 times a cross-width dimension.

A shaped composite collagen product includes soluble and insoluble collagen components and may be lyophilized by freezing such as to below 0° C. and in some cases cryogenically freezing to a temperature of about −150° C. (−238° F.) to absolute zero −273° C. (−460° F.).

Forming a collagen hydrogel at neutral pH at a temperature between 32° C. and 39° C. and preferably about 37° C. for about 1 minute to about 60 minutes and preferably about 30 minutes. The hydrogel may be frozen before lyophilization. A shaped composite article may be formed during forming a collagen hydrogel.

A shaped composite article may be made by casting the composite collagen including soluble and insoluble components, in a shaped mold with desired dimensions, solid or hollow. The composite collagen may be formed into a hydrogel by being neutralized for pH and incubated at a temperature from about 4° C. to 40° C. while in the mold to create a shaped composite article. The composite collagen may be frozen before or after forming the shaped composite article and may be lyophilized before or after being frozen. The composite collagen may be frozen with or without neutralization of the pH. The shaped composite article may be lyophilized after being shaped in said mold without freezing. The composite collagen may be lyophilized before or after freezing or before or after being formed into a hydrogel. The shaped composite article will have a free-standing shape, wherein the shape is retained without support.

The ratio of the soluble to insoluble collagen components may be varied through the thickness of the composite collagen product, wherein a first layer or an outer layer has a ratio of soluble collagen to insoluble collagen that is at least about 25% different from a ratio of soluble collagen to insoluble collagen on a second layer, such as an inner layer, opposite the outer layer, for example. The difference in the ratio of soluble collagen to insoluble collagen from a first layer to a second layer may be 50% or more, about 100% or more, about 200% or more, about 500% or more and any range between and including the percentages provided. As an example, a collagen patch may be configured with a low ratio of soluble to insoluble collagen on the outer layer to slow degradation from the exposed surface but may have a high ratio of soluble to insoluble collagen on an inside layer to enable fixation to a biological surface for example, such as tissue or an organ and the percentage difference in the ratios may be about 100% or more.

Prior to separating, the extract collagen may be removed from solution as an integral composite collagen product which may be further dried and lyophilized are required for the application.

The extracted collagen may be in an extracted collagen solution having both the soluble and insoluble collagen combined but in different phases within the solution or separated by density or specific gravity within the solution. An extracted collagen solution may undergo centrifugation to physically separate the soluble from the insoluble collagen.

The extracted collagen may further undergo salt precipitation to isolate type I soluble collagen. This process may include:
  a. Adding salt (such as sodium chloride (NaCl)) to the soluble collagen solution to induce collagen precipitation;
  b. Agitating the salt with added soluble collagen solution for at least 1 hour to ensure uniform salt distribution and precipitation;
  c. Centrifuging the precipitated soluble collagen solution from step (b) to collect pellet containing Type I soluble collagen;
  d. Dissolving the pellet from step (c) in acid (such as acetic acid or hydrochloric acid) for at least 2 hours to solubilize type I soluble collagen; and
  e. Dialyzing the acid dissolved pellet from step (d) against $H_2O$ with the temperature of $H_2O$ between 2-20° C. for at least 1 day to produce a purified type I soluble collagen solution.

In the salt precipitation process for the production of type I soluble collagen, the molarity of the salt may be between 0.1 M to 5 M, and may be about 0.1M or more, about 0.5M or more, about 1M or more, about 2.5M or more, or 5M or less and any range between and including the values provided. Also, the molarity of acid in the salt precipitation process may be between 0.005 M to 5 M, such as about 0.005M or more, about 0.1M or more, about 1M or more, about 2.5M or more, or 5M or less and any range between and including the values provided.

In the process for the production of type I soluble collagen, the dialysis step may involve using a dialysis bag with a molecular weight cutoff (MWCO) ranging from 1 kDa to 100 kDa, such as about 1 kDa or more, about 25 kDa or more, about 50 kDa or more, about 75 kDa or more, about 100 kDa or less and any range between and including the values provided.

The purity of type I soluble collagen produced in through the precipitation process may be between 80% to 100%.

The type I soluble collagen may further undergo lyophilization which includes freezing the soluble type I collagen solution and may also include heating the frozen soluble type I collagen solution to a lyophilization temperature of at least 10° C. (50° F.) and drawing vacuum on the soluble type I soluble collagen, wherein a vacuum pressure is at least 100 m Torr.

The soluble collagen may by methacrylated, a chemical process, wherein the functional groups, such as the carboxylic acid groups of a protein are exchanged with methacrylate anhydride. In this way the protein chains or groups may be combined to make a tougher composition.

Methacrylated, collagen may be neutralized in pH and then a photoinitiator may be added at varying concentration and then it may be exposed to UV light such as from 300 nm to 600 nm for about 1 minute to about 30 minutes at a temperature of about 4 to 40° C. The hydrogel may be incubated at a temperature from about 4 to 40° C. The hydrogel may be frozen before lyophilization. A shaped composite article may be formed during incubation of the methacrylated collagen hydrogel.

The type I soluble collagen may further undergo methacrylation which may include the following steps:
  a. providing a methacrylic anhydride solution;
  b. combining the lyophilized type I soluble collagen with an acid (such as acetic acid or hydrochloric acid) to produce a type I soluble collagen solution;
  c. adding base (such as Tris-HCl) to the type I soluble collagen solution from step (b) to produce a non-pH adjusted solution;
  d. providing buffer (such as NaOH) and adding said buffer to the type I soluble collagen solution from step (c) to adjust the pH of the solution to between 7.0 and 8.0, producing a pH adjusted type I soluble collagen solution;
  e. adding the methacrylic anhydride solution to the pH adjusted type I soluble collagen solution to produce a type I soluble collagen methacrylic anhydride solution;
  f. agitating the pH adjusted type I soluble collagen methacrylic anhydride solution for a methacrylation time of at least 2 hours and in a temperature range of 0° C. to 20° C.;
  g. centrifuging the pH-adjusted type I soluble collagen methacrylic anhydride solution from step (f) to collect supernatant containing type I soluble collagen methacrylate; and
  h. dialyzing the supernatant containing type I soluble collagen methacrylate from step (g) against acid for at least 1 day to produce methacrylated type I soluble collagen.

In the methacrylation process, the molarity of acid may be between 0.005 M to 5 M, such as about 0.005M or more, about 0.1M or more, about 1M or more, about 2.5M or more, or about 5M or less and any range between and including the values provided.

In the methacrylation process, the molecular weight cutoff (MWCO) may range from ranging from 1 kDa to 100 kDa.

In the methacrylation process, a degree of methacrylation of the methacrylated type I soluble collagen produced in step (h) may be between 10% to 95%. The degree of methacrylation may be optimized for a particular application or for specific properties of a shaped composite product. A higher degree of methacrylation may produce a composite product with greater strength. Optimization or variation in degree of methacrylation may be accomplished by changing the concentration of the methacrylic anhydride, changing the reaction time of collagen and methacrylic anhydride, and/or by adjusting the pH of the collagen and methacrylic anhydride solution.

The methacrylation process may be controlled to produce a methacrylated type I soluble collagen with desired mechanical properties, including stiffness, elasticity, and degradation rate which may be adjusted by controlling the degree of methacrylation.

The methacrylated soluble type I collagen solution from step (h), may further undergo lyophilization by freezing the methacrylated soluble type I collagen solution then heating the frozen methacrylated soluble type I collagen solution to a lyophilization temperature of at least 10° C. (50° F.) and drawing vacuum on the methacrylated soluble type I collagen, wherein a vacuum pressure is at least 100 mTorr.

Once the product is lyophilized, the material may be reconstituted the by combining with acid. The purity of the collagen can then be determined using SDS-PAGE, for example. SDS-Page (sodium dodecyl sulfate-polyacrylamide gel electrophoresis) is a discontinuous electrophoretic system developed by Ulrich K. Laemmli and is used as a method to separate proteins with molecular masses between 5 and 250 kDa.

A soluble collagen product, as defined herein, will dissolve in 1 mM of acetic to 1000 mM, having a pH of between about 0.5 pH to 4.0 pH within about one week.

An insoluble collagen, as defined herein, will not dissolve in 1 mM of acetic to 1000 mM, having a pH of between about 0.5 pH to 4.0 pH within a week and will maintain a shape such as a sheet of material after one week.

A minced dermis tissue, as used herein, is dermis tissue that is cut into pieces, such as having dimensions of about 25 mm or less, about 15 mm or less, or about 10 mm or less, about 5 mm or less, and any range between and including the values provided.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
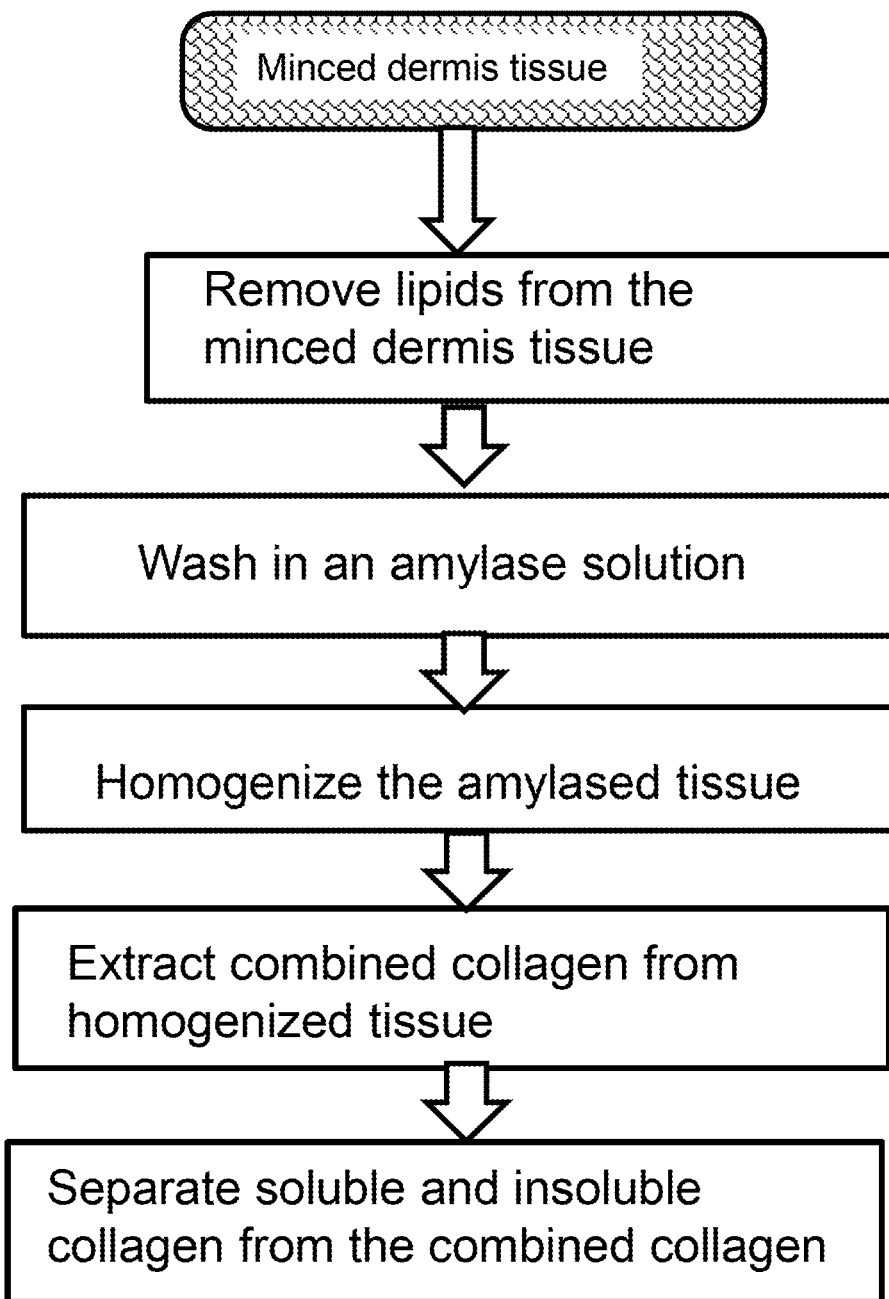
FIG. 1 shows a flow diagram of an exemplary process for the production of a soluble collagen product and an insoluble collagen product from mammalian dermis tissue.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, the process for the production of a soluble collagen product and an insoluble collagen product from mammalian dermis tissue includes washing in an amylase solution and homogenizing the tissue under cold conditions. The collagen is then extracted from the homogenized tissue and subsequently separated such as by centrifugation.

Figure 2:
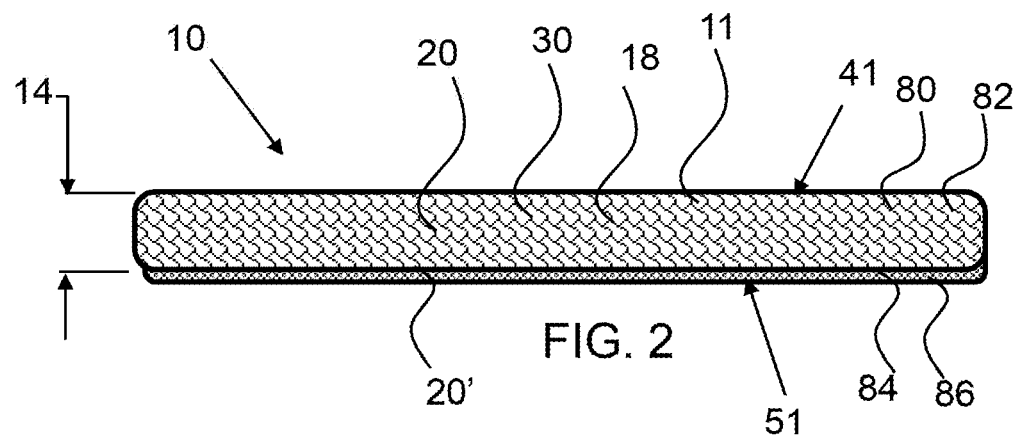
FIG. 2 shows a composite collagen product having a ratio of soluble collagen to insoluble collagen.

As shown in FIG. 2, a composite collagen product 10 is composed of a single layer having a thickness 14. A composite collagen product 10 may be a membrane, having a thickness of less than 1 mm and forming a thin sheet of material. The composition of the layer of the collagen product can be controlled by changing the concentration of soluble collagen 20 to insoluble collagen 30. A composite collagen product 10 can be composed of two or multiple layers of composite collagen product and can be tailored by changing the ratio of soluble to insoluble collagen. A plurality of membranes of composite collagen product may be layered. The composite collagen 11 has a first surface 41 and an opposing second surface 51. This is a sheet of composite collagen, and the properties may vary from the first surface to the second surface. The composite collagen product 10 includes collagen fibers 18 and as described herein, these collagen fibers may be oriented in a particular direction or may be randomly oriented. The composite collagen product 10 may have a first ratio of soluble collagen 20 to insoluble collagen 30 on or proximal to the first surface and a second ratio of soluble collagen 20' to insoluble collagen on or proximal to the second surface 51.

Figure 3:
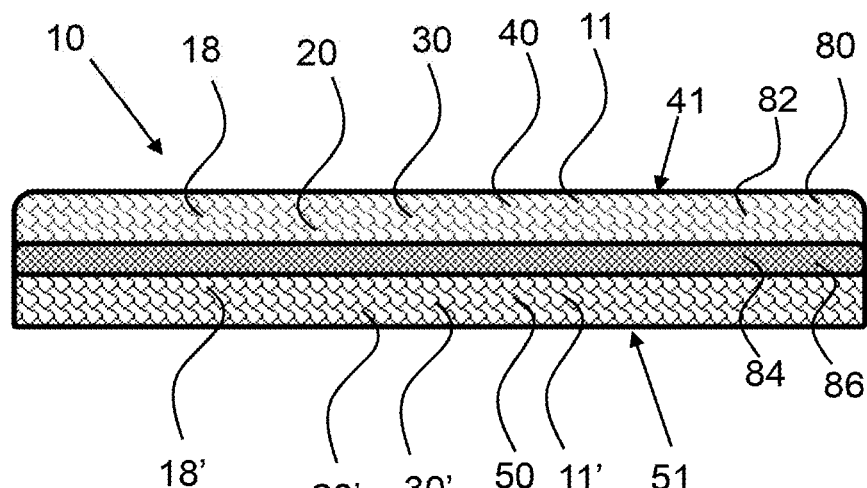
FIG. 3 shows a composite collagen product having a ratio of soluble collagen to insoluble collagen and multiple layers of composite collagen.

As shown in FIG. 3, a composite collagen product 10 has a ratio of soluble collagen 20 to insoluble collagen 30 that may be tailored for a given application. As shown, the composite collagen product has a first layer 40 of composite collagen 11 having a first ratio of soluble collagen 20 to insoluble collagen 30 and a second layer 50 of composite collagen 11' having a second ratio of soluble collagen 20' to insoluble collagen 30'. The first layer 40 of composite collagen 11 extends to or is on the first surface 41 and the second layer 50 of composite collagen 11' extends to or is on the second surface 51. Note that one or more additional layers of composite collagen may be configured between the first layer 40 and second layer 50.

The first layer 40 may be oriented in alignment with the second layer and/or the additive sheet 86. The collagen fibers of the first layer may be configured an offset angle to the collagen fibers in the second layer, or to a feature of the additive, such as fiber or strand or weave orientation. An offset angle may be about 20 degrees or more, about 45 degrees or more, about 60 degrees or more, about 75 degrees or more or about orthogonal, or 90 degrees. In an exemplary embodiment the collagen fibers of the first layer are configured orthogonal, about 90 degrees from collagen fibers of the second layer. A composite collagen product may have a plurality of layers of composite collagen product and each layer may be configured an offset angle, such as about 90 degrees from each adjacent layer. As described herein the collagen fibers of a composite collagen product may be oriented through processing such as by stretching and locked into position during freezing, lyophilization and/or cross-linking.

The collagen fibers 18 and 18' may be oriented in different directions, wherein the first collagen fibers 18 of the first layer 40 of composite collagen 11 are oriented at an offset angle to the collagen fibers 18' of the second layer 50 of composite collagen 11'. The offset angle may be 10 degrees or more, about 22.5 degrees or more, about 45 degrees or more, or about 90 degrees or more, or orthogonal. An orthogonal orientation may provide a higher composite strength in the composite collagen product 10.

Referring to FIGS. 2 and 3, a shaped collagen product may be formed with different properties through the thickness of the sheet or from a first side or first surface 41 to a second side or second surface 51. For example, the first side may have a larger pore size or structure than the pore size or structure of a second side. A first side may have a rough texture while a second side may be substantially smoother than said first side. These changes in the structure may be controlled by freezing parameters, molding parameters, composition and structure and materials of the mold, and lyophilization parameters. The mold may have a rough or smooth surface, for example. The collagen fibers in a shaped composite collagen product may be aligned or randomly oriented by controlling the freezing parameters, molding parameters, composition and structure of materials of the mold, and/or lyophilization parameters. A shaped composite collagen product having aligned collagen fibers may be stronger along the oriented axis of the collagen fibers than a randomly oriented or non-aligned shaped composite collagen product.

A shaped composite collagen product may include an additive 80, which may be an integral additive 82, such as particles, fibers or chemical compounds that are mixed with the composite collagen or may be an additive product 84, such as an additive sheet 86, a thin layer of additive material, or tube or other form or shaped material that the collagen is combined with, such as by coating or imbibing into or coupling thereto. An additive may be an organic material, such as elastin, dermis or synthetic material, such as a polymeric support scaffold, including a microporous support scaffold, porous membrane, polyethylene, polytetrafluoroethylene. A polymer may include a homopolymer, co-polymer and may be a thermoplastic or thermoset material. An additive 80, such as an additive product 84 and particularly an additive sheet 86 may be a bioresorbable material such as a bioresorbable polymer. A bioresorbable material is resorbed by the body when implanted, such as by enzymatic breakdown, pH, temperature, physical breakdown and the like. An additive may be fibers that may be an integral additive and mixed in with the composite collagen or may form a layer on a surface of a composite collagen product. Fibers may be bundled and may be aligned for increased strength and the collagen may coat or be coupled to the fibers. Also, fibers may be configured as a layer with a composite collagen product and again, the fibers in this layer may be oriented or in a random orientation. Fibers may be organic fibers, a bioresorbable fiber or a synthetic fiber, for example.

Referring to FIGS. 2 and 3, the composite collagen product 10 includes an additive 80 as described herein. An integral additive 82 is combined with the composite collagen product 10 and may be mixed with and extend throughout the composite collage product. An additive product 84 forms a layer on the second surface 51 and may be an additive sheet 86, a planar layer which may have pores and wherein the collagen may extend into these pores. As shown in FIG. 3, the additive sheet 86 is configured within the composite collagen product 10, with composite collagen product on either side of the additive sheet. An additive sheet may be a bioresorbable material, a dermis material, a synthetic membrane and the like.

A composite collagen product 10 having a plurality of layers, may be coupled together, wherein an first layer 40 is coupled to a second layer 50 by an adhesive, suturing, compressing such as free compression wherein the composite collagen product is unrestrained around a perimeter, or compression within a restrain, glueing, fusing including pressing with heat and the like.

Figure 4:
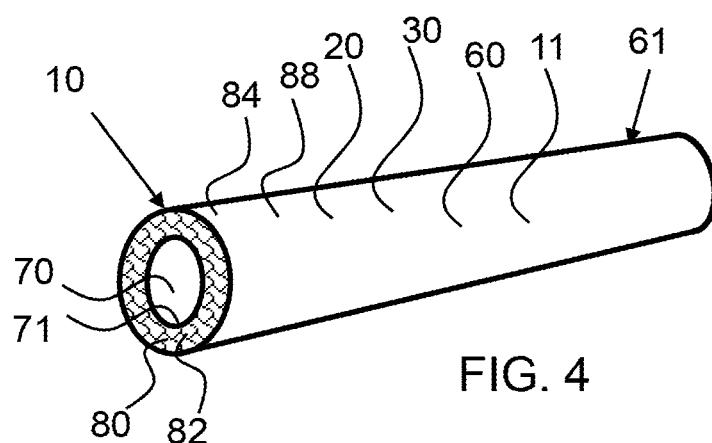
FIG. 4 shows a composite collagen product shaped or formed into a tube.

As shown in FIG. 4, a composite collagen product 10 has a ratio of soluble collagen 20 to insoluble collagen 30 that may be tailored for a given application. As shown, the composite collagen product is formed or shaped into a tube 60, having an aperture 70 extending through the tube and an outside surface 61 and interior surface 71 within the tube. The tube may be cylindrical in shape as shown or polygonal on the outside surface and/or interior surface. The composite collagen product 10 includes an additive 80 as described herein. An integral additive 82 is combined with the composite collagen product 10 and may be mixed with and extend throughout the composite collage product. An additive product 84 forms a layer on the outside surface 61 and may be an additive sheet 86 that is wrapped around the composite collagen product 10 to form an additive tube 88 around the composite collagen product 10.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A process for the methacrylation of a soluble collagen from an extracted collagen from mammalian dermis tissue comprising:
   a) providing said extracted collagen including said soluble collagen and an insoluble collagen;
   b) salt precipitation of the soluble collagen to isolate a type I soluble collagen and further comprising methacrylation of the type I soluble collagen, comprising:
   c) providing a methacrylic anhydride solution:
   d) combining the type I soluble collagen with an acid to produce a type I soluble collagen solution;
   wherein the molarity of acid is between 0.005 M to 5 M;
   e) adding base to the type I soluble collagen solution to produce a non-pH adjusted collagen solution;
   f) providing buffer and adding said buffer to the non-pH adjusted collagen solution to adjust the pH between 7.0 and 8.0, producing a pH adjusted type I soluble collagen solution;
   g) adding the methacrylic anhydride solution to the pH adjusted type I soluble collagen solution to produce a type I soluble collagen methacrylic anhydride solution:
   h) agitating the type I soluble collagen methacrylic anhydride solution for a methacrylation time of at least 2 hours at a temperature between 0° C. to 20° C.;
   i) centrifuging the type I soluble collagen methacrylic anhydride solution from step (h) to collect supernatant containing type I soluble collagen methacrylate; and
   j) dialyzing the supernatant containing type I soluble collagen methacrylate against acid for at least 1 day to produce methacrylated type I soluble collagen:
   k) lyophilization of the methacrylated soluble type I collagen comprising freezing the methacrylated soluble type I collagen and then heating the frozen methacrylated soluble type I collagen to a lyophilization temperature of at least 10° C. (50° F.) while drawing vacuum on the methacrylated soluble type I collagen, wherein a vacuum pressure is at least 100 mTorr:
   wherein a degree of methacrylation of the methacrylated type I soluble collagen produced is between 10% to 95%.

2. The process of claim 1, wherein the minced mammalian dermis tissue has a size of no more than 10 mm.

3. The process of claim 1, wherein the dialysis further comprises providing a dialysis bag with a molecular weight cutoff (MWCO) ranging from 1 kDa to 100 kDa and passing the supernatant containing type I soluble collagen methacrylate through said dialysis bag.

* * * * *